United States Patent [19]

MacLeod et al.

[11] Patent Number: 5,506,257
[45] Date of Patent: Apr. 9, 1996

[54] AMINOCYCLOHEXYLAMIDES FOR ANTIARRHYTHMIC AND ANAESTHETIC USES

[75] Inventors: Bernard A. MacLeod; Michael J. A. Walker; Richard A. Wall, all of Vancouver, Canada

[73] Assignee: University of British Columbia, Vancouver, Canada

[21] Appl. No.: 196,865

[22] Filed: Feb. 15, 1994

Related U.S. Application Data

[63] Continuation-in-part of Ser. No. 42,427, Mar. 26, 1993, abandoned, which is a continuation-in-part of Ser. No. 858,060, Mar. 26, 1992, abandoned.

[51] Int. Cl.$^6$ .......................... A61K 31/38; A61K 31/40
[52] U.S. Cl. .......................... 514/422; 514/213; 514/409; 514/428; 514/429; 514/613; 514/617; 514/212; 514/233.5; 514/235.2; 514/235.8; 514/237.8; 514/307; 514/319; 514/323; 514/324; 514/412; 514/414; 514/432; 514/438; 514/443; 514/444; 514/451; 514/462; 514/469
[58] Field of Search .................................. 514/213, 409, 514/428, 429, 613, 617, 422

[56] References Cited

U.S. PATENT DOCUMENTS

| | | |
|---|---|---|
| 4,438,130 | 3/1984 | Kaplan . |
| 4,508,911 | 4/1985 | Kaplan . |
| 4,579,863 | 4/1986 | Horwell et al. . |
| 4,598,087 | 7/1986 | Horwell . |
| 4,656,182 | 4/1987 | Horwell . |
| 4,663,343 | 5/1987 | Horwell . |
| 4,677,122 | 6/1987 | Horwell . |
| 4,737,493 | 4/1988 | Horwell . |

FOREIGN PATENT DOCUMENTS

| | | |
|---|---|---|
| 0146297 | 6/1985 | European Pat. Off. . |
| 0147085 | 7/1985 | European Pat. Off. . |
| 0207773 | 1/1987 | European Pat. Off. . |
| 0372466 | 6/1990 | European Pat. Off. . |
| 0380063 | 8/1990 | European Pat. Off. . |
| WO86/07257 | 12/1986 | WIPO . |

OTHER PUBLICATIONS

Abraham et al., "Antiarrhythmic Properties of Tetrodotoxin Against Occlusion–Induced Arrhythmias in the Rat: A Novel Approach to the Study of the Antiarrhythmic Effects of Ventricular Sodium Channel Blockade," *J. Pharmacol. Exp. Ther.* 251:1166–1173, 1989.

Alzheimer and Ten Bruggencate, "Nonopioid Actions of the κ–Opioid Receptor Agonists, U 50488H and U 69593, on Electrophysiologic Properties of Hippocampal CA3 Neurons in Vitro," *J. Pharmacol. Exp. Ther.* 255:900–905, 1990.

Clark et al., "Highly Selective κ Opioid Analgesics. Synthesis and Structure–Activity Relationships of Novel N–[2–Aminocyclohexyl)aryl]acetamide and N–[(2–Aminocyclohexyl)aryloxy]acetamide Derivatives," *J. Med. Chem.* 31:831–836, 1988.

Clark et al., "PD117302: a selective agonist for the κ–opioid receptor," *Br. J. Pharmacol.* 93:618–626, 1988.

Curtis and Walker, "Quantification of arrhythmias using scoring systems: an examination of seven scores in an in vivo model of regional myocardial ischaemia," *Cardiovasc. Res.* 22:656–665, 1988.

Halfpenny et al., "Highly Selective κ–Opioid Analgesics. 2. Synthesis and Structure–Activity Relationships of Novel N–[(2–Aminocyclohexyl)aryl]acetamide Derivatives," *J. Med. Chem.* 32:1620–1626, 1989.

Halfpenny et al., "Highly Selective κ–Opioid Analgesics. 3. Synthesis and Structure–Activity Relationships of Novel N–[2–(1–Pyrrolidinyl)–4– or –5–substituted–cyclohexyl] arylacetamide Derivatives," *J. Med. Chem.* 33:286–291, 1990.

Howard and Walker, "Electrical Stimulation Studies with Quinacainol, a Putative 1C Agent, in the Anaesthetised Rat," *Proc. West. Pharmacol. Soc.* 33:123–127, 1990.

Hunter et al., "CI–977, a novel and selective agonist for the κ–opioid receptor," *Br. J. Pharmacol.* 101:183–189, 1990.

Leighton et al., "Pharmacological profile of PD 117302, a selective κ–opioid agonist," *Br. J. Pharmacol.* 92:915–922, 1987.

Ma et al., "Synthesis and analgesic activity of analogs of U–50488, an opiate kappa–agonist," *Chemical Abstracts* 117::48285, p. 906, 1992.

Meecham et al., "An in vitro profile of activity for the (+) and (–) enantiomers of spiradoline and PD117302," *Eur. J. Pharmacol.* 173:151–157, 1989.

Penz et al., "A New ECG Measure (RSh) for Detecting Possible Sodium Channel Blockade in Vivo in Rats," *J. Pharmacol. Methods* 27:51–58, 1992.

Pugsley et al., "Antiarrhythmic effects of U–50, 488H in rats subject to coronary artery occlusion," *Eur. J. Pharmacol.* 212:15–19, 1992.

Pugsley et al, "Cardiovascular actions of the κ–agonist, U–50, 488H, in the absence and presence of opioid receptor blockade" *Br. J. Pharmacol.* 105:521–526, 1992.

Pugsley et al., "Electrophysiological and antiarrhythmic actions of the κ agonist PD 129290, and its R,R(+) –enantiomer, PD 129289," *Br. J. Pharmacol.* 110:1579–1585, 1993.

Pugsley et al., "Cardiovascular Actions of U50, 488H, and Related Kappa Agonists," *Cardiovascular Drug Reviews* 11:151–164, 1993.

Sarne et al., "Anti–arrhythmic activities of opioid agonists and antagonists and their stereoisomers," *Br. J. Pharmacol.* 102:696–698, 1991.

Singh et al., "The anticonvulsant action of CI–977, a selective κ–opioid receptor agonist: a possible involvement of the glycine/NMDA receptor complex," *Eur. J. Pharmacol.* 191:477–480, 1990.

(List continued on next page.)

*Primary Examiner*—Rebecca Cook
*Attorney, Agent, or Firm*—Seed and Berry

[57] ABSTRACT

The present invention provides methods for blocking sodium channels in cardiac or neuronal tissue using aminocyclohexylamides. This invention also provides kits including aminocyclohexylamides and instructions for the use of the compounds for the treatment of arrhythmia or for the inducement of local anaesthesia.

15 Claims, No Drawings

OTHER PUBLICATIONS

Sitsapesan and Parratt, "The effects of drugs interacting with opioid receptors on the early ventricular arrhythmias arising from myocardial ischaemia," *Br. J. Pharmacol.* 97:795–800, 1989.

Szmuszkovicz and Von Voigtlander, "Benzeneacetamide Amines: Structurally Novel Non-Mµ Opioids," *J. Med Chem.* 25:1125–1126, 1982.

Von Voigtlander et al., "U–50,488: A Selective and Structurally Novel Non–Mu (Kappa) Opioid Agonist," *J. Pharmacol. Exp. Ther.* 224:7–12, 1983.

Wong et al., "Effects of Drugs Interacting with Opioid Receptors During Normal Perfusion or Ischemia and Reperfusion in the Isolated Rat Heart–an Attempt to Identify Cardiac Opioid Receptor Subtype(s) Involved in Arrhythmogenesis," *J. Mol. Cell. Cardiol.* 22:1167–1175, 1990.

AMINOCYCLOHEXYLAMIDES FOR ANTIARRHYTHMIC AND ANAESTHETIC USES

CROSS REFERENCE TO RELATED APPLICATION

This application is a continuation-in-part application to Ser. No. 042,427, filed Mar. 26, 1993, abandoned which is a continuation-in-part application to Ser. No. 858,060, filed Mar. 26, 1992, abandoned.

TECHNICAL FIELD

The present invention relates generally to the use of aminocyclohexamide compounds to block cardiac and neuronal sodium channels. This invention is more particularly related to the treatment of cardiac arrhythmias and the inducement of local anaesthesia through the use of aminocyclohexylamide compounds that block cardiac and neuronal sodium channels, respectively.

BACKGROUND OF THE INVENTION

Compounds that block sodium channels in the membranes of cardiac or neuronal tissues are known. For example, Class I antiarrhythmic compounds, such as lidocaine, will block membrane channels for sodium ions in cardiac tissue. A subset of such antiarrhythmic compounds (known as Class Ia antiarrhythmics) includes quinidine and procainamide which are capable of blocking potassium channels in cardiac tissue in addition to blocking sodium channels. Such antiarrhythmic compounds will also block sodium channels in neuronal tissue which is a property of a local anaesthetic compound.

Class I antiarrhythmic compounds may be used to treat supraventricular arrhythmias and ventricular arrhythmias. Treatment of ventricular arrhythmia is very important since such an arrhythmia, especially ventricular fibrillation, can be fatal. Serious ventricular arrhythmias (ventricular tachycardia and ventricular fibrillation) occur most often in the presence of myocardial ischemia and/or infarction. Ventricular fibrillation often occurs in the setting of acute myocardial ischemia, before infarction fully develops. At present, lidocaine is the current drug of choice for prevention of ventricular fibrillation. However, many Class I antiarrhythmic compounds may actually increase mortality in patients who have had a myocardial infarction. Therefore, there is a need in the art to identify new antiarrhythmic treatments, particularly treatments for ventricular arrhythmias. The present invention fills the need, and further provides other related advantages.

It has been suggested that opioid antagonists, such as naloxone or opioid agonists, may interact with sodium channels and have antiarrhythmic activity. However, the opioid activity is probably separate from any such antiarrhythmic activity, as the former activity appears to be stereospecific but the latter activity is not (Sarne, Y., et al. (1991) *Brit. J. Pharmacol.*, 102:696–698).

International patent application WO 86/07257 published Dec. 18, 1986, suggested an antiarrhythmic utility for certain aminocycloalkylamide compounds previously known to be analgesics. One such compound is known as U-50,488H and has been shown to be an opioid agonist particularly active at the kappa receptor (Von Voightlander, P. F., et al. (1983) *J. Pharmacol. Exp. Ther.*, 244:7–12). It has also been suggested that U-50,488H may have a local anaesthetic activity by reducing sodium conductance (Alzheimer, C. and Ten Bruggencate, G. (1990) *J. Pharmacol. Exp. Ther.*, 255:900–905). The analgesic and local anaesthetic properties of U-50,488H are antagonized by the kappa opioid antagonist, naloxone. However, other researchers have been unable to demonstrate any significant antiarrhythmic activity of U-50,488H (Sitsapesan, R., and Parratt, J. R. (1989) *Br. J. Pharmacol.*, 97:795–800) and, it has been predicted that U-50,488H is actually arrhythmogenic (Wong, T. M., et al. (1990) *J. Mol. Cell Cardiol.*, 22:1167–1175).

A different group of analgesic aminocyclohexylamide compounds are described in Horwell's U.S. Pat. Nos. 4,579,863; 4,598,087; 4,656,182; 4,663,343; 4,737,493; and 4,855,316. The opioid activity of these compounds is antagonized by naloxone and is stereospecific with respect to the enantiomers at the amine and amide substituents of the cyclohexyl ring (see: Meecham, K. G., et al. (1989) *Eur. J. Pharmacol.*, 73:151–157; Singh, L. et al. (1990) *Eur. J. Pharmacol.*, 191:477–480; and Hunter, J. C., et al. (1990) *Br. J. pharmacol.*, 101:183–189).

SUMMARY OF THE INVENTION

Briefly stated, the present invention provides a method for blocking sodium channels in cardiac or neuronal tissue comprising administering an effective amount of an enantiomer or geometric isomer of a compound of formula I, or a pharmaceutically acceptable salt thereof, the compound of the formula:

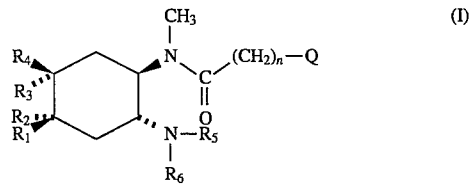

n is either 0 or 1; $R_1$, $R_2$, $R_3$, $R_4$ are hydrogen, hydroxy, alkoxy of from one to four carbon atoms, or points of attachment of a spiro- or fused five- or six-membered heterocyclic ring containing one oxygen or sulfur atom; $R_5$ and $R_6$ are either alkyl of from one to five carbon atoms or, when taken together with the nitrogen atom to which they are attached, form a pyrrolidinyl, piperidinyl, morpholinyl, tetrahydroisoquinolinyl, or hexahydroazepinyl ring; and Q is selected from the group of substituents comprising: 3,4,5-trimethylphenoxy;

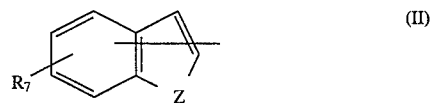

where $R_7$ is hydrogen, fluorine, chlorine, alkyl of from one to six carbon atoms, or aryl; Z is —$CH_2$—, —O—, —S—, or N—$R_8$ where $R_8$ is hydrogen, alkanoyl of from one to six carbon atoms, or alkyl of from one to six carbon atoms;

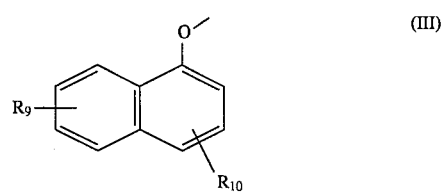

where $R_9$ and $R_{10}$ are independently hydrogen, fluorine, bromine, alkyl of from one to six carbon atoms, or alkoxy of from one to four carbon atoms;

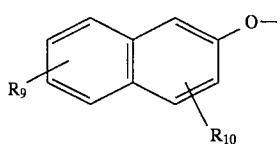

(IV)

where $R_9$ and $R_{10}$ are defined as above; and

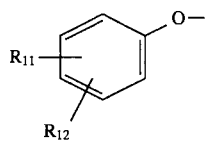

(V)

where $R_{11}$ and $R_{12}$ are independently hydrogen, fluorine, chlorine, bromine, nitro, trifluoromethyl, alkyl of from one to six carbon atoms, alkoxy of from one to six carbon atoms, or aryl.

In another aspect, the present invention provides a kit comprising a pharmaceutically acceptable carrier or diluent, instructions for the treatment of arrhythmia or for the inducement of local anaesthesia, and at least one compound of formula I as described above or a pharmaceutically acceptable salt thereof.

DETAILED DESCRIPTION OF THE INVENTION

The disclosure of the present invention shows that a group of aminocyclohexylamide compounds, including those described in certain United States patents to Horwell, will block sodium channels in cardiac and neuronal tissue. This activity appears to be independent of the opioid agonist activity of the compounds, as the sodium blocking activity is not antagonized by naloxone. This activity is very potent in respect of cardiac tissue and, thus, the compounds are useful as antiarrhythmic agents. As compared to known antiarrhythmic agents, these compounds are particularly potent, effective and fast acting. At higher concentrations, the compounds also block sodium channels locally in neuronal tissue and have a quick onset of action which results in the compounds being useful as local anaesthetic agents. In addition, since the ability of the compounds to block sodium channels is not stereospecific, enantiomers of the compounds may be selected than have the desired sodium blocking activity, but have significantly reduced kappa agonist activity.

Compounds of formula I, as depicted above, constitute a class of substituted aminocyclohexamide compounds. One nitrogen atom is an amine nitrogen substituted with $R_5$ and $R_6$ as defined above. Preferably, $R_5$ is methyl and $R_6$ is a lower alkyl, most preferably methyl, or, when taken together with the nitrogen atom to which they are attached, $R_5$ and $R_6$ preferably form a pyrrolidinyl ring, a morpholinyl ring or a hexahydroazepinyl ring. The other nitrogen atom is an N-methylamide substituted as described above, wherein n is preferably 1.

Preferably $R_1$ and $R_4$ are hydrogen or, $R_3$ and $R_4$ are hydrogen and $R_1$ and $R_2$ are an oxaspiran ring.

As used herein, the term "aryl" means phenyl; phenyl substituted with alkyl of from one to four carbon atoms, alkoxy of from one to four carbon atoms, nitro, or trifluromethyl; 2- or 3-thienyl; and, 2- or 3-thienyl substituted with alkyl of from one to four carbon atoms or alkoxy of from one to four carbon atoms.

In formula II depicted above, the bond that links the substituent with the remainder of the compound of formula I is shown as intersecting both rings of the fused ring structure of the substituent II. This indicates that the bond may be at any one of the carbon atoms in the fused ring structure except at the position of $R_7$.

While a compound of the present invention is depicted above in formula I by a structural formula having a particular isomeric form, such structural formula contains one or more asymmetric carbon atoms and therefore exists in various stereoisomeric forms. In addition, the compound is capable of existing in different geometric isomeric forms. For example, the substituent $R_1$ of the cyclohexane ring may be positioned on the same side of the average plane of the ring as the amide nitrogen, or on the side opposite. The present invention contemplates the use of all geometric and stereoisomeric forms of the compounds of formula I.

Compounds of formula I may be used in the present invention as individual enantiomers, as racemic mixtures or, as combinations of different substituted compounds of formula I. Examples of individual enantiomers include compounds 2 and 7 below. racemic mixtures include compounds 1 and 6 below.

The following compounds of formula I are preferred:
1. (±)-trans-N-methyl-N-[2-(1-pyrrolidinyl)cyclohexyl] benzo[b]thiophene-4-acetamide;
2. (1R,2R)-(+)-N-methyl-N-[2-(1-pyrrolidinyl)cyclohexyl] benzo[b]thiophene-4-acetamide;
3. [(±)-(1α,2β,4β,5β)]-N-methyl-N-[4,5-dimethoxy-2-(1-pyrrolidinyl)cyclohexyl]benzo[b]thiophene-4-acetamide;
4. [(±)-(1α,2β,4β,5β)]-N-methyl-N-[4,5-dimethoxy-2-(1-pyrrolidinyl)cyclohexyl](3,4-dichlorophenoxy)acetamide;
5. (±)-trans-N-methyl-N-[2-(1-hexahydroazepinyl)cyclohexyl](3,4-dichlorophenoxy)acetamide;
6. (±)-trans-N-methyl-N-[7-(1-pyrrolidinyl)-1-oxaspiro[4.5]dec-8-yl]benzo[b]furan-4-acetamide;
7. [5R(5α,7β,8β)]-N-methyl-N-[7-(1-pyrrolidinyl)-1-oxaspiro[4.5]dec-8-yl]benzo[b]furan-4-acetamide;
8. (±)-trans-N-methyl-N-[2-(1-pyrrolidinyl)cyclohexyl](3,4-dichlorophenoxy)acetamide;
9. (±)-trans-N-methyl-N-[2-(1-pyrrolidinyl)cyclohexyl] benzo[b]thiophene-3-acetamide;
10. [5S (5α,7β,8β)]-N-methyl-N-[7-(1-pyrrolidinyl)-1-oxaspiro[4.5]dec-8-yl]benzo [b]furan-4-acetamide;
11. (1S,2S)-2-(benzo[b]thiophene-4-yl)-N-methyl-N-[2-(1-pyrrolidinyl)cyclohexyl]acetamide;
12. (1R,2R)-2-(indol-3-yl)-N-methyl-N-[2-(1-pyrrolidinyl)cyclohexyl]acetamide;
13. (1S,2S)-2-(indol-3-yl)-N-methyl-N-[2-(1-pyrrolidinyl)cyclohexyl]acetamide;
14. (1R,2R)-2-(2,3-dichlorophenoxy)-N-methyl-N-[2-(1-pyrrolidinyl)cyclohexyl]acetamide;
15. (1S,2S)-2-(2,3-dichlorophenoxy)-N-methyl-N-[2-(1-pyrrolidinyl)cyclohexyl]acetamide;
16. (1R,2R)-N-methyl-2-(1-naphthalenyloxy)-N-[2-(1-pyrrolidinyl)cyclohexyl]acetamide;
17. (1S,2S)-N-methyl-2-(1-naphthalenyloxy)-N-[2-(1-pyrrolidinyl)cyclohexyl]acetamide;
18. [1S(1α,2β,4β)]-N-methyl-N-[4-methoxy-2-(1-pyrrolidinyl)cyclohexyl]benzo[b]furan-4-acetamide;
19. [1R(1α,2β,4β)]-N-methyl-N-[4-methoxy-2-(1-pyrrolidinyl)cyclohexyl]benzo[b]furan-4-acetamide;
20. (1R,2R)-inden-2-yl-N-methyl-N-[2-(1,1-dimethylamino)cyclohexyl]carboxamide; and
21. (1S,2S)-inden-2-yl-N-methyl-N-[2-(1,1-dimethylamino)cyclohexyl]carboxamide.

The compounds of formula I may be prepared by known methods, including those described in the aforementioned United States patents to Horwell (which are incorporated herein in their entirety by reference). Suitable methods for the synthesis of diaminocyclohexane intermediates useful for preparation of a variety of compounds identified above are described in Szmuszkovicz, J., and Von Voightlander, P. F. (1982) *J. Med. Chem.*, 25:1125–1126. The oxaspiro and methoxy-cyclohexanediamine intermediates useful for syntheses of compounds 7, 10, 18, and 19 are described in Halfpenny, P. R., et al. (1990) *J. Med. Chem.*, 33:286–291. Preparation or sources of the carboxylic acids used in the final stage of the syntheses of the compounds listed above are also to be found in the above references as well as in Clark, C. R., et al. (1988) *J. Med Chem.*, 31:831–836. The above latter three references contain information on all the steps of the syntheses of the compounds listed above, and provide sufficient guidance to a person skilled in the art to repeat the synthesis, isolation, and purification of these and many other analogous compounds. The individual enantiomers are obtained, if desired, from mixtures of the different forms by known methods of resolution, such as the formation of diastereomers, followed by recrystallisation.

The following compounds are particularly preferred as antiarrhythmics:

(±)-trans-N-methyl-N-[2-(1-pyrrolidinyl)cyclohexyl]benzo[b]thiophene-4-acetamide;

(1R,2R)-(±)-N-methyl-N-[2-(1-pyrrolidinyl)cyclohexyl]benzo[b]thiophene-4-acetamide;

[(±)-(1α,2β,4β,5β)]-N-methyl-N-[4,5-dimethoxy-2-(1-pyrrolidinyl)cyclohexyl]benzo[b]thiophene-4-acetamide;

[(±)-(1α,2β,4β,5β)]-N-methyl-N-[4,5-dimethoxy-2-(1-pyrrolidinyl)cyclohexyl](3,4-dichlorophenoxy)acetamide; and (±)-trans-N-methyl-N-[2-(1-hexahydroazepinyl)cyclohexyl](3,4-dichlorophenoxy)acetamide.

It is most preferable that the compounds of formula I selected for use in the present invention be those enantiomers that lack kappa opioid activity or wherein such activity is significantly reduced. For this purpose, the stereoisomeric form illustrated in formula I above is preferred. The following enantiomers having reduced kappa opioid activity are preferred:

[5S(5α,7β,8β)]-N-methyl-N-[7-(1-pyrrolidinyl)-1-oxaspiro[4.5]dec-8-yl]-benzo[b]furan-4-acetamide;

(1S,2S)-2-(benzo[b]thiophen-4-yl)-N-methyl-N-[2-(1-pyrrolidinyl)cyclohexyl]acetamide;

(1R,2R)-2-(indol-3-yl)-N-methyl-N-[2-(1-pyrrolidinyl)cyclohexyl]acetamide;

(1R,2R)-2-(2,3-dichlorophenoxy)-N-methyl-N-[2-(1-pyrrolidinyl)cyclohexyl]acetamide;

(1R,2R)-N-methyl-2-(1-naphthalenyloxy)-N-[2-(1-pyrrolidinyl)cyclohexyl]acetamide;

[1S(1α,2β,4β)-N-methyl-N-[4-methoxy-2-(1-pyrrolidinyl)cyclohexyl]benzo[b] furan-4-acetamide; and (1R,2R)-inden-2-yl-N-methyl-N-[2-(1,1-dimethylamino)cyclohexyl]carboxamide.

The compounds of formula I may be in the form of a pharmaceutically acceptable acid addition salt. Such salts include the hydrochloride, sulfate, phosphate, citrate, and other salts known in the art. Pharmaceutical compositions of compound I or salts of compound I may contain pharmaceutically acceptable carriers or diluents, which are well known in the art.

In order to assess whether a compound has the required pharmacological activity within the present invention, it may be subjected to a series of tests. In the first of such tests, a compound is given as increasing (doubling with each dose) intravenous boluses every 8 minutes to a pentobarbital anesthetized rat. The effects of the compound on blood pressure, heart rate and the ECG are measured 30 seconds and 8 minutes after each dose. Increasing doses are given until the animal dies. The cause of death is identified as being of respiratory or cardiac origin. This test gives an indication as to whether the compound is blocking sodium channels and/or potassium channels, and in addition gives information about acute toxicity. The indices of sodium channel blockade are increasing P-R interval and QRS widening of the ECG. Potassium channel blockade results in Q–T interval prolongation of the ECG.

A second test involves administration of a compound as an infusion to pentobarbital anesthetized rats in which the left ventricle is exposed to electrical square wave stimulation performed according to a preset protocol described in detail further below. This protocol includes the determination of thresholds for induction of extrasystoles and ventricular fibrillation. In addition, effects on electrical refractoriness are assessed by a single extra beat technique. In addition, effects on blood pressure, heart rate and the ECG are recorded. In this test, sodium channel blockers produce the ECG changes expected from the first test. In addition, sodium channel blockers also raise the thresholds for induction of extrasystoles and ventricular fibrillation. Potassium channel blockade is revealed by increasing refractoriness and widening of the Q–T intervals of the ECG.

A third test involves exposing isolated rat hearts to increasing concentrations of a compound. Ventricular pressures, heart rate and ECG are recorded in the isolated heart in the presence of varying concentrations of the compound. This test provides evidence for direct toxic effects on the myocardium. Concentrations found to be effective in this test are expected to be efficacious in the electrophysiological studies.

A fourth test is estimation of the antiarrhythmic activity of a compound against the arrhythmias induced by coronary artery occlusion in anaesthetized rats. It is expected that a good antiarrhythmic compound will have antiarrhythmic activity at doses which have minimal effects on either the ECG, blood pressure or heart rate.

A compound may also be tested directly for effects on sodium and potassium currents in isolated rat myocytes. Isolated rat myocytes are obtained in the conventional manner used to obtain isolated myocytes from isolated hearts. They are used in conventional voltage clamp studies. In order to obtain adequate voltage clamps for estimation of a compound's effects on sodium and potassium currents, the whole-cell patch clamp technique is used. In this technique, a microelectrode is attached to a cell in such a manner that the cell's internal contents are in free communication with the electrode's content. Using the appropriate buffers and conventional voltage step protocols, both sodium and potassium currents can be identified. The effects of a compound are tested on these currents.

All of the foregoing tests are performed using rat tissue. In order to ensure that a compound is not having effects which are only specific to rat tissue, further experiments are performed in dogs and primates. In order to assess possible sodium channel and potassium channel blocking actions in vivo in dogs, a compound is tested for effects on the ECG, ventricular epicardial conduction velocity and responses to electrical stimulation. An anesthetized dog is subjected to an open chest procedure to expose the left ventricular epicardium. After the pericardium is removed from the heart a recording/stimulation electrode is sewn onto the epicardial surface of the left ventricle. Using this array, and suitable stimulation protocols, conduction velocity across the epicardium as well as responsiveness to electrical stimulation can be assessed. This information coupled with measurements of the ECG allows one to assess whether sodium and/or potassium channel blockade occurs. As in the first test in rats, a compound is given as a series of increasing bolus doses. At the same time, possible toxic effects of a compound on the dog's cardiovascular system is assessed.

The effects of a compound on the ECG and responses to electrical stimulation are also assessed in intact halothane anesthetized baboons (*Papio anubis*). In this preparation, a blood pressure cannula and ECG electrodes are suitably placed in an anesthetized baboon. In addition, a stimulating electrode is placed into the right ventricle, together with a monophasic action potential electrode. As in the tests described above, ECG and electrical stimulation responses to a compound reveal the possible presence of sodium and/or potassium channel blockade. The monophasic action potential also reveals whether a compound widens the action potential, an action expected of a potassium channel blocker.

The present invention may be employed to treat the rhythm of a heart or prevent arrhythmias occurring in a heart that is susceptible to arrhythmia. Methods of administering effective amounts of antiarrhythmic agents are well known in the art and include the administration of an oral or parenteral dosage form. Such dosage forms include, but are not limited to, parenteral solutions, tablets, capsules, sustained release implants, and transdermal delivery systems. Generally, oral or intravenous administration is preferred. The dosage amount and frequency is selected to create an effective level of the agent without harmful effects. It will generally range from a dosage of from about 0.1 to about 100 mg/kg/day, and typically from about 0.1 to 10 mg/kg where administered orally or intravenously for antiarrhythmic effect. A 0.1% to 1% solution injected into a local site is typical for use as a local anaesthetic.

When the present invention is employed to induce local anaesthesia, the means of administration may be the same as described above in the case of treatment of arrhythmia, except that use of oral administration in the form of tablets or capsules will generally not be appropriate. Topical application of the local anaesthetic agent, for example in the form of an ointment or an aerosol spray, may be employed. Means of administering local anaesthetics are well known in the art.

Administration of this invention may be carried out in combination with the administration of other agents. For example, it may be desired to administer an opioid antagonist, such as naloxone, if a compound of formula I administered according to the present invention has not been selected from those enantiomers having reduced kappa opioid activity. The naloxone may antagonize opioid activity of the administered compound without adverse interference with the antiarrhythmic activity.

The present invention also includes a commercial kit containing a pharmaceutical composition which includes one or more compounds of formula I or, pharmaceutically acceptable salts thereof, in addition to any desired, pharmaceutically acceptable, carriers or diluents. The commercial kit also includes instructions for the use of the pharmaceutical composition for the treatment of arrhythmia or for the inducement of local anaesthesia. Preferably the commercial package will contain one or more unit doses of the pharmaceutical composition. For example, such a unit dose may be an amount sufficient for the preparation of an intravenous injection. It will be evident to those in the art that compounds which are light and/or air sensitive may require special packaging and/or formulation. For example, packaging may be used which is opaque to light, and/or sealed from contact with ambient air, and/or formulated with suitable coatings or excipients.

The following examples are offered by way of illustration and not by way of limitation.

EXAMPLES

In the following examples, reference will be made to tests of a compound which is identified by name and the source of the compound tested, as follows:
U-50,488H:
trans-N-methyl-N-[2-(1-pyrrolidinyl)cyclohexyl]-3,4-dichlorophenylacetamide; UpJohn Company.

In the following examples, antiarrhythmic efficacy was assessed against coronary occlusion induced arrhythmias in the rat using standard methods. ECG and electrophysiological stimulating tests in rats and primates involved standard ECG leads and ventricular stimulation (implanted electrodes in the rats and inserted right ventricular electrodes in primates). Intracellular recordings were made from the epicardium of rat hearts in vivo. Whole cell voltage clamp studies were performed in single, isolated, adult rat heart cells.

In the above array of tests, the compounds for use in this invention were typically found to be more than ten times as potent as some other Class I antiarrhythmics such as mexilitine (Igwemezie, et al. (1992) *European Journal of Pharmacology*, 210:271–277), disopyramide, procainamide, and quinacainol (Penz, et al. (1992) *Journal of Pharmacological Methods*, 27:51–58). The compounds for use in this invention were equipotent with the extremely toxic tetrodotoxin (Abraham, et al. (1990) *J. Pharmacol. Exp. Ther.*, 251:1166–1173), which is a potent blocker of the cardiac sodium channel. However, the compounds for use in this invention did not exhibit the neuronal toxicity of tetrodotoxin or even that of lidocaine. No overt signs of anaesthesia resulted when the compounds were injected intravenously at antiarrhythmic doses. Thus, the present invention may be used to treat arrhythmia, for example, by injection of the compound, without producing anaesthesia. However, the compounds may also be administered locally to induce a local anaesthetic effect.

It is estimated that the $LD_{50}$ of compound 10 in rats is 16 µmol/kg. For compound 1, the estimated $LD_{50}$ values in rats is 32 µmol/kg and in mice is 27 µmol/kg. Toxic symptoms of doses exceeding what is required for antiarrhythmic activity include fall in blood pressure or heart rate, and alteration of asystole/idioventricular rhythms. The bradycardic and hypotensive effects of the compounds suitable for this invention seem to be consistent with type I antiarrhythmic compounds but, the neuronal toxicity appears to be less than that of compounds such as lidocaine.

EXAMPLE 1 trans-N-methyl-2-(1-pyrrolidinyl)cyclohexanamine

This compound was prepared based on the method in U.S. Pat. No. 4,579,863.

(i) Cyclohexene oxide (202 mL, 2 mol) was added dropwise to aqueous methyl amine (466 mL or 40% solution, 6 mol) over 70 minutes. After a further 90 minutes, the temperature of the reaction mixture was 48° C. and was reduced to 30° C. by cooling in a water bath. After a further 2 hours, the mixture had returned to room temperature. It was stirred overnight, and then refluxed for 3 h. The mixture was saturated with sodium hydroxide (cooled during addition), extracted several times with diethyl ether (total 500 mL), the diethyl ether layer dried over sodium sulphate overnight, and the diethyl ether removed on a rotary evaporator. The remaining diethyl ether and cyclohexene oxide were removed by partial vacuum distillation. Distillation under full vacuum yielded a colorless fraction boiling at 95° C., (±)-trans-2-(methylamino)cyclohexanol: 217 g (84%).

(ii) A mixture of (±)-trans-2-(methylamino)cyclohexanol (200 g, 1.55 mol) and diethyl ether (400 mL) in a 3 L beaker was stirred and cooled in an ice bath as chlorosulfonic acid (103 mL, 1.55 mol) was added dropwise. After approximately 25 mL had been added, it was necessary to stir the thick mixture with a spatula, and after a further 40 mL of acid had been added more diethyl ether (200 mL) was added. The whole addition took 105 minutes. The sticky mixture was stirred by hand and left at room temperature for 2.5 hours. The mixture was filtered, and the solid washed with diethyl ether (300 mL). A solution of sodium hydroxide pellets (216 g) in water (1 L) was cooled in an ice bath, and then added slowly to the cooled solid. The mixture because less viscous and the addition was complete within 20 minutes. The mixture was left to stand overnight, then poured into a 2 L flask and steam distilled, with water being added from a dropping funnel to maintain constant volume in the distillation pot. After the diethyl ether had distilled, an organic product co-distilled with the water at a head temperature of 92°–100° C. (600 mL of a 2-phase colorless mixture was collected), to leave a small quantity of dark amber material on the surface of the water remaining in the distillation pot. The distillate was saturated with sodium hydroxide and extracted with diethyl ether (8×100 mL), the diethyl ether layer dried over sodium sulphate and the diethyl ether removed on a rotary evaporator to leave crude product (133 g) which was distilled under reduced pressure to give 7-methyl-7-azabicyclo[4.1.0]heptane (77.9 g, 43%).

(iii) A solution of ammonium chloride (1.6 g) in water (100 mL) was added to 7-methyl-7-azabicyclo [4.1.0] heptane (70 g, 0.59 mol) under nitrogen. pyrrolidine (210 mL, 2.5 mol) was added and the mixture was stirred and refluxed under nitrogen for 20 hours. Sodium hydroxide was added to saturate the aqueous phase and the mixture was extracted with diethyl ether (7×100 mL). The combined organic extracts were washed with water (2×10 mL), and dried over sodium sulphate. The diethyl ether was removed on a rotary evaporator and excess pyrrolidine (60 mL) was distilled off under low vacuum. The product, (±)-trans-N-methyl-N-[2-(1-pyrrolidinyl)cyclohexyl]amine, was distilled under full vacuum (46°–48° C.). Yield 86 g (77%).

EXAMPLE 2

(±)-trans-N-methyl-N-[2-(1-pyrrolidinyl)cyclohexyl] benzo[b]thiophene-4-acetamide monohydrochloride This compound was prepared according to the procedure described by C. R. Clark et al. in *J. Med. Chem.* 31:831–836, 1988. A solution of 4-thianaphtheneacetyl chloride (prepared by refluxing 4-thianaphtheneacetic acid (1.94 g, 10 mmol) with excess thionyl chloride) in dichloromethane (10 mL) was added dropwise to a solution of (±)-trans-N-methyl-N-[2-(1-pyrrolidinyl)cyclohexyl]amine prepared in Example 1 (1.84 g, 10 mmol) in dichloromethane (10 mL) at 0° C. After stirring at room temperature for 10 minutes, diethyl ether was added until no further precipitate resulted. The crude product was collected by filtration, washed with diethyl ether and dried in vacuo. It was recrystallised from methanol/diethyl ether, to give the title compound, 3.3 g (85%). Proton and carbon-13 NMR data in accord.

Elemental analysis: Calcd. for $C_{21}H_{29}N_2OClS$: C 64.18, H 7.44%, N 7.13%; Found C 63.34, H 7.17, N 7.10.

EXAMPLE 3

(±)-trans-N-methyl-N-[2-(1-pyrrolidinyl)cyclohexyl] (3,4-dichlorophenoxy)acetamide monohydrochloride The title compound was prepared according to the method described in Example 2, using 3,4-dichlorophenoxyacetic acid (2.34 g, 11 mmol) and (±)-trans-N-methyl-N-[2-(1-pyrrolidinyl)cyclohexyl]amine prepared in Example 1 (2 g, 11 mmol). The crude product, which started to precipitate before the addition of the diethyl ether, was recrystallised from hot dichloromethane. Yield 2.9 g (62%).

Elemental analysis: Calcd. for $C_{19}H_{27}N_2O_2Cl_3 \cdot CH_2Cl_2$: C 47.41, H 5.77, N 5.53 Cl 34.98%; Found C 47.86, H 5.79, N 5.53, Cl 35.96%.

EXAMPLE 4

(±)-trans-N-methyl-N-[2-(1-pyrrolidinyl)cyclohexyl] benzo[b]thiophene-3-acetamide monohydrochloride The title compound was prepared according to the method described in Example 2, using 3-thianaphtheneacetic acid (4.24 g, 22 mmol) and (±)-trans-N-methyl-N-[2-(1-pyrrolidinyl)cyclohexyl]amine prepared in Example 1 (3.85 g, 21 mmol) . The crude product, which started to precipitate before the addition of the diethyl ether, was recrystallised from hot methanol/diethyl ether to yield a white solid, 6.54 g (79%).

Elemental analysis: Calcd. for $C_{21}H_{29}N_2OClS$: C 64.18, H 7.44, N 7.13%; Found C 63.16, H 7.40, N 6.99%.

EXAMPLE 5

Resolution of (±)-trans-N-methyl-N-[2-(1-pyrrolidinyl)cyclohexyl] amine

The resolution is based on a modification of the method reported by C. R. Clark et al. in *J. Med. Chem.* 31:831–836, 1988. The (−)-enantiomer (R,R) of trans-N-methyl-N-[2-(1-pyrrolidinyl)cyclohexyl]amine prepared in Example 1 was separated by repeated fractional crystallization of the 2,3-di-p-toluoyl-D-tartaric acid salts. A solution of (±)-trans-N-methyl-N-[2-(1-pyrrolidinyl)cyclohexyl] amine (16 g, 88 mmol) in boiling methanol (400 mL) was treated with a solution of 2,3-di-p-toluoyl-D-tartaric acid (35.6 g, 88 mmol) in boiling methanol (400 mL). The solution was cooled to 30° C. and the resulting solid was collected by filtration. The above process was repeated for two further portions of racemic diamine (16 g each), and the three batches of solid (total 101 g, $[\alpha]^{20}_D(CH_2Cl_2)$ −68° for free diamine) which were isolated were combined and washed with boiling methanol (1 L) . The washed solid (78 g, $[\alpha]^{20}_D$ $(CH_2Cl_2)$ −82° for free diamine) was divided into batches (approx. 5 g each), and each batch was recrystallised from boiling methanol (600 mL). The first crops (total 33.9 g, $[\alpha]^{20}_D$ $(CH_2CL_2)$ −93.2° for free diamine) were filtered off after allowing the methanol solutions to stand at room temperature for 3–4 hours. The second crops (total 9.25 g,

[α]$^{20}_D$ (CH$_2$Cl$_2$) −92.6° for free diamine) were isolated from the filtrate after standing in the fridge overnight. The two crops were combined and converted to the free diamine by partitioning between dichloromethane and aqueous (20%) potassium hydroxide solution. The dichloromethane layer was dried and evaporated, and the residue was partitioned between diethyl ether and aqueous (10%) potassium hydroxide solution. The diethyl ether layer was dried and evaporated to give the product, (1R, 2R)-(−)-N-methyl-N-[2-(1-pyrrolidinyl)cyclohexyl]amine, as a pale yellow oil 14.3 g (60%); [α]$^{20}_D$ (CH$_2$Cl$_2$) −92.9°.

EXAMPLE 6

(1R,2R)-(+)-N-methyl-N-[2-(1-pyrrolidinyl) cyclohexyl]benzo[b]thiophene-4-acetamide monohydrochloride The title compound was prepared according to the method described in Example 2, using 4-thianaphtheneacetic acid (2.28 g, 12 mmol) and (1R,2R)-(−)-N-methyl-N-[2-(1-pyrrolidinyl)cyclohexyl]amine isolated using the resolution method described in Example 5 (2.21 g, 12 mmol). The title compound (the (+)-enantiomer of the racemate prepared in Example 2) was recrystallised from hot methanol. Yield 3.26 g, (69%) . [α]$^{20}_D$ (CH$_2$Cl$_2$) +29.3°. Proton and carbon-13 NMR data in accord.

Elemental analysis: Calcd. for C$_{21}$H$_{29}$N$_2$OClS: C 64.18, H 7.44%, N 7.13%; Found C 61.49, H 7.45, N 6.72%.

EXAMPLE 7

[(±)-(1α,2β,4β,5β)]-N-methyl-N-[4,5-dimethoxy-2-(1-pyrrolidinyl)cyclohexyl]amine The starting material, [(±)-(1α,2β,4β,5β)]-[4,5-dimethoxy-2-(1-pyrrolidinyl)]cyclohexanol, was prepared according to the procedure described in U.S. Pat. No. 4,855,316. This was converted to the title compound as follows:

A solution of [(±)-(1α,2β,4β,5β)]-[4,5-dimethoxy-2-(1-pyrrolidinyl)cyclohexanol (7 g, 30.5 mmol) and triethylamine (4.8 mL, 35 mmol) in dichloromethane (70 mL) under nitrogen was cooled in an ice-bath as methanesulfonyl chloride (2.55 mL, 33 mmol) in dichloromethane (35 mL) was added dropwise. After 1 hour at 0° C., GC showed the reaction to be complete. The mixture was diluted with dichloromethane (70 mL) and washed with water (2×50 mL). The aqueous phase was washed with dichloromethane (20 mL) and the organic fractions were combined and dried over sodium sulphate. The solvent was removed in vacuo to leave a yellow oil. An aqueous solution of methylamine (50 mL of a 40% solution, 0.57 mol) was added to the mesylated product, and the mixture refluxed for a total of 1.5 hours. The reaction mixture was partitioned between 10% sodium hydroxide solution (150 mL) and dichloromethane (150 mL). The aqueous layer was washed with dichloromethane (150 mL) and the combined organic layers were dried over sodium sulphate. The solvent was removed to leave the product as a yellow oil. Yield 7 g (95%). Proton and carbon-13 NMR data in accord.

EXAMPLE 8

[(±)-(1α,2β,4β,5β)]-N-methyl-N-[4,5-dimethoxy-2-(1-pyrrolidinyl)cyclohexyl]benzo[b]thiophene-4-acetamide monohydrochloride The title compound was prepared according to the method described in Example 2, using 4-thianaphtheneacetic acid (0.78 g, 4 mmol) and [(±)-(1α,2β,4β,5β)]-N-methyl-N-[4,5-dimethoxy-2-(1-pyrrolidinyl)cyclohexyl]amine prepared in Example 7 (1 g, 4 mmol). The product was recrystallised from hot methanol/diethyl ether.

Elemental analysis: Calcd. for C$_{23}$H$_{33}$N$_2$O$_3$ClS: C 60.98, H 7.43, N 6.18; Found C 60.79, H 7.30, N 6.13%.

EXAMPLE 9

[(±)-(1α,2β,4β,5β)]-N-methyl-N-[4,5-dimethoxy-2-(1-pyrrolidinyl)cyclohexyl](3,4-dichlorophenoxy) acetamide monohydrochloride The title compound was prepared according to the method described in Example 2, using 3,4-dichlorophenoxyacetic acid (0.91 g, 4 mmol) and (±)-( 1α,2β,4β,5β)]-N-methyl-N-[4,5-dimethoxy-2-(1-pyrrolidinyl)cyclohexyl]amine prepared in Example 7 (1 g, 4 mmol). The product was washed with diethyl ether. Yield 1.2 g (60%).

Elemental analysis: Calcd. for C$_{21}$H$_{31}$N$_2$O$_4$Cl$_3$: C 52.35, H 6.48, N 5.81%, Found C 52.15, H 6.52, N 5.75%.

EXAMPLE 10

(±)-trans-N-methyl-N-[2-(1-hexahydroazepinyl) cyclohexyl]amine (i) Hexamethyleneimine (17.3 mL, 0.15 mol), cyclohexene oxide (15.5 mL, 0.15 mol) and water ( 5 mL) were refluxed under nitrogen overnight. GC analysis showed the reaction to be complete. The cooled mixture was partitioned between saturated sodium hydroxide solution (50 mL) and diethyl ether (75 mL). The aqueous layer was washed with diethyl ether (30 mL), and the combined diethyl ether layers were dried over sodium sulphate. The diethyl ether was removed from the amber solution on a rotary evaporator. The crude product, (±)-trans-[2-(1 -hexahydroazepinyl)]cyclohexanol (28 g), was purified by full vacuum distillation (62°–65° C.) 23 g (76%).

(ii) A solution of (±)-trans-[2-(1-hexahydroazepinyl)]cyclohexanol prepared above (17 g, 86 mmol) and triethylamine (13.5 mL, 97 mmol) in dichloromethane (135 mL) under nitrogen was cooled in an ice-bath as methanesulfonyl chloride (7.25 mL, 93 mmol) in dichloromethane (70 mL) was added dropwise. After 50 minutes at 0° C., GC showed the reaction to be complete. The mixture was diluted with dichloromethane (135 mL) and washed with water (2×135 mL). The aqueous phase was washed with dichloromethane (70 mL) and the organic fractions were combined and dried over sodium sulphate. The solvent was removed in vacuo to leave a yellow oil (19.7 g) An aqueous solution of methylamine (140 mL of a 40% solution, 1.6 mol) was added to the mesylated product, and the mixture refluxed for a total of 5.5 h. The reaction mixture was partitioned between 10% sodium hydroxide solution (335 mL) and dichloromethane (335 mL). The aqueous layer was washed with dichloromethane (200 mL) and the combined organic layers were dried over sodium sulphate. The solvent was removed to leave the crude product as a yellow oil. This was distilled under full vacuum (bp 103°–105° C.) to give the title diamine as a colorless liquid. Yield 15.5 g (86%).

EXAMPLE 11

(±)-trans-N-methyl-N-[2-(1-hexahydroazepinyl) cyclohexyl](3,4-dichlorophenoxy)acetamide monohydrochloride The title compound was prepared according to the method described in Example 2, using 3,4-dichlorophenoxyacetic acid (2.15 g, 10 mmol) and (±)-trans-N-methyl-N-[2-(1- hexahydroazepinyl)cyclohexyl]amine prepared in Example 10 (2 g, 10 mmol). The crude product, which precipitated without the addition of any diethyl ether, was recrystallised from hot methanol (150 mL). Yield 3.58 g (80%).

Elemental analysis: Calcd. for $C_{21}H_{31}N_2O_2Cl_3$: C 56.07, H 6.95, N 6.23 Cl 23.64%; Found C 55.29, H 7.20, N 6.02, Cl 23.84%.

EXAMPLE 12

(±)-trans-N-methyl-N-[2-(4-morpholinyl)cyclohexyl] amine (i) The intermediate aminoalcohol, (±)-trans-[2-(4-morpholinyl)]cyclohexanol, was prepared by the method detailed in Example 10(i), refluxing morpholine (15 mL, 172 mmol), cyclohexene oxide (17.4 mL, 172 mmol) and water (5 mL) for 2.5 h. The crude product was purified by full vacuum distillation (bp 92°–93 ° C.) to give a clear liquid which solidified on cooling. Yield 27 g (85%).

(ii) The aminoalcohol (15 g, 81 mmol) was converted to the title compound using the method detailed in Example 10(ii), using triethylamine (13 mL, 94 mmol) and methanesulfonyl chloride (7 mL, 90 mmol), followed by treatment (1 hour reflux) with aqueous methylamine (150 mL of a 40% solution, 1.4 mol). The title product, which was not distilled, was obtained as a pale yellow oil which crystallized overnight. Yield 15.6 g (97%).

EXAMPLE 13

(±)-trans-N-methyl-N-[2-(4-morpholinyl)cyclohexyl] (3,4-dichlorophenoxy)acetamide monohydrochloride The title compound was prepared according to the method described in Example 2, using 3,4-dichlorophenoxyacetic acid (2.51 g, 11 mmol), and (±)-trans-N-methyl-N-[2-(4-morpholinyl)cyclohexyl]amine prepared in Example 12 (2 g, 10 mmol). The crude product, which precipitated without the addition of any diethyl ether, was recrystallised from hot methanol. Yield 3.42 g (78%). Proton and carbon-13 NMR data in accord.

Elemental analysis: Calcd. for $C_{19}H_{27}N_2O_3Cl_3$: C 52.13, H 6.22, N 6.40%; Found C 52.10, H 6.12, N 6.38%.

EXAMPLE 14

(±)-trans-N-methyl-N-[2-(4-morpholinyl)cyclohexyl] benzo[b]thiophene-3-acetamide monohydrochloride The title compound was prepared according to the method described in Example 2, using 3-thianaphtheneacetic acid (5.05 g, 26.3 mmol) and (±)-trans-N-methyl-N-[2-(4-morpholinyl)cyclohexyl]amine prepared in Example 12 (5 g, 25.3 mmol). The product was recrystallised from hot methanol (250 mL), and washed with ether. Yield 5.81 g (56%). Proton and carbon-13 NMR data in accord.

Elemental analysis: Calcd. for $C_{21}H_{29}N_2O_2ClS$: C 61.67, H 7.15, N 6.85%; Found C 61.41, H 7.05, N 6.79%.

EXAMPLE 15

(±)-trans-N-methyl-N-{2-[bis(2-methoxyethyl)amino] cyclohexyl}amine (i) The intermediate aminoalcohol, (±)-trans-{-2-[bis(2-methoxyethyl)amino]}cyclohexanol, was prepared by the method detailed in Example 10(i), refluxing bis(2-methoxyethyl)amine (25 mL, 169 mmol), cyclohexene oxide (17.2 mL, 170 mmol) and water (8 mL) for 30 h. The crude product was purified by full vacuum distillation (bp 83°–85° C.) to give a clear liquid. Yield 29.3 g, (75%).

(ii) The aminoalcohol (15 g, 65 mmol) was converted to the title compound using the method detailed in Example 10(ii), using triethylamine (9.8 mL, 70 mmol) and methanesulfonyl chloride (5.6 mL, 72.4 mmol), followed by treatment (3 hour reflux) with aqueous methylamine (110 mL of a 40% solution). The crude product was distilled under full vacuum (bp 72°–78° C.) to give the title diamine as a colorless oil. Yield 11 g (69%).

EXAMPLE 16

(±)-trans-N-methyl-N-{2-[bis(2-methoxyethyl)amino]cyclohexyl}(3,4-dichlorophenoxy)acetamide monohydrochloride The title compound was prepared according to the method described in Example 2, using 3,4-dichlorophenoxyacetic acid (2.14 g, 9.7 mmol) and (±)-trans-N-methyl-N-{2-bis(2-methoxyethyl)amino]cyclohexyl}amine prepared in Example 15 (2.25 g, 9.2 mmol). The crude product was recrystallised from hot methanol. Yield 2.9 g (65%). Carbon-13 NMR data in accord.

Elemental analysis: Calcd. for $C_{21}H_{33}N_2O_4Cl_3$: C 52.13, H 6.87, N 5.79%; Found C 51.99, H 6.93, N 5.81%.

EXAMPLE 17

(±)-trans-N-methyl-N-[2-(1,2,3,4-tetrahydroisoquinolinyl)cyclohexyl]amine (i) The intermediate aminoalcohol, (±)-trans-[ 2-(1,2,3,4-tetrahydroisoquinolinyl)cyclohexanol, was prepared by the method detailed in Example 10(i), refluxing 1,2,3,4-tetrahydroisoquinoline (10 mL, 79.9 mmol), cyclohexene oxide (8.1 mL, 80 mmol) and water (4 mL) for 10 h. The crude product was purified by full vacuum distillation (bp 105°–106° C.) to give a viscous pale yellow oil. Yield 14.7 g, (57%).

(ii) The aminoalcohol (14.2 g, 61.5 mmol) was converted to the title compound using the method detailed in Example 10(ii), using triethylamine (9.3 mL, 66.7 mmol) and methanesulfonyl chloride (5.2 mL, 67.2 mmol), followed by treatment (3 hour reflux) with aqueous methylamine (1102 mL of a 40% solution, 1.23 mol). The crude product was distilled under full vacuum (bp 113°–119° C.) to give the title diamine as a yellow oil. Yield 11 g (73%).

EXAMPLE 18

(±)-trans-N-methyl-N-[2-(1,2,3,4-tetrahydroisoquinolinyl)cyclohexyl](3,4-dichlorophenoxy)acetamide monohydrochloride The title compound was prepared according to the method described in Example 2, using 3,4-dichlorophenoxyacetic acid (2.14 g, 9.7 mmol) and (±)-trans-N-methyl-N-[2-(1,2, 3,4-tetrahydroisoquinolinyl)cyclohexyl]amine prepared in Example 17 (2.25 g, 9.2 mmol). The crude product was recrystallised from hot methanol, to give the title compound which was slightly hygroscopic. Yield 3.19 g (72%). Carbon-13 NMR data in accord.

Elemental analysis: Calcd. for $C_{24}H_{29}N_2O_2Cl_3$: C 59.58, H 6.04, N 5.79%; Found C 57.69, H 6.14, N 5.56%.

EXAMPLE 19

Antiarrhythmic efficacy was assessed by investigating the activity of the compounds on the incidence of cardiac arrhythmias in pentobarbital anaesthetized rats subject to coronary artery occlusion. Rats weighing 150–200 gm were subjected to preparative surgery and assigned to groups in a random block design. In each case, the trachea was cannulated and the animals were artificially ventilated. The left carotid artery was cannulated for measurement of mean arterial blood pressure and withdrawal of blood samples. The right jugular vein was also cannulated for injection of drugs. The thoracic cavity was opened and a polyethylene occluder loosely placed around the left anterior descending coronary artery. ECG was recorded by insertion of electrodes placed along the anatomical axis of the heart determined by palpation. In random and double-blind manner, rats were given an initial injection of saline or, 8 μmol/kg naloxone hydrochloride (Dupont Pharmaceutical Co.). A second injection of saline vehicle, or the compound to be tested at various doses, was given 5 minutes later. All drugs were dissolved in 0.9% NaCl solution. Thereafter, the occluder was pulled so as to produce coronary artery occlusion. ECG, arrhythmias, blood pressure, heart rate on mortality were monitored for 30 minutes after occlusion. Arrhythmias were recorded as ventricular tachycardia (VT) and ventricular fibrillation (VF) and according to Curtis, M. J. and Walker, M. J. A. (1988) *Cardiovasc. Res.*, 22:656. Rats were excluded from the study if they did not exhibit pre-occlusion serum potassium concentrations within the range of 2.9–3.9 mM; occlusion associated with increases in R-wave height and "S-T" segment elevation; and, an occluded zone (measured after death by cardiogreen dye perfusion) in the range of 25–50% of total left-ventricular weight.

Table 1 describes the result of tests of the compounds described therein as ED50 values which are the doses required to produce 50% reductions in the arrhythmic activity referred to therein. Initial results with compound 7 showed that at 2 and 8 μmol/kg, the incidents of fatal arrhythmias (VF) was reduced to 25% and 0%, 1.5 respectively, from a control value of 88%. Naloxone alone slightly decreased the incidence of VF arrhythmias. Pretreatment with naloxone did not antagonize the activity of the compounds shown in Table 1. The doses of U-50,488H and compound 7 required for significant antiarrhythmic effects exceeded the doses required for kappa agonism for those compounds. These results demonstrate that the compounds useful within this invention are significantly more potent antiarrhythmic agents than U-50,488H, especially in respect of fatal arrhythmias (VF). Therefore, the former compounds have a much more useful therapeutic ratio (which compares efficacy to toxicity) than U-50,488H.

TABLE 1

| Activity | Compound 10 | Compound 7 | U-50,488H |
| --- | --- | --- | --- |
| VT | 6 | 8 | 16 |
| VF | 1 | <1 | 6 |

EXAMPLE 20

The procedures described in Example 19 were carried out and measurements taken before coronary artery occlusion. Table 2 describes blood pressure (BP), heart rate (HR), and EKG (PR; QRS; and, QT intervals) effects of compound 7 at 2 and 8 μmol/kg in the presence and absence of naloxone (8 μmol/kg). Values are the mean ±sem in pentobarbital anaesthetized rats (n=8), and * indicates P<0.05 of differences from control. Measurements were made 10 minutes after the end of drug administration.

Compound 7 prolonged P–R interval and QRS width as well as depressing blood pressure and heart rate in a manner generally unaffected by naloxone. This is evidence that the compound causes sodium channel blockade in a manner independent of its kappa opioid agonist activity.

TABLE 2

| Treatment Initial: Final: | saline saline | naloxone saline | saline Cmpd. 7 | saline Cmpd. 7 | naloxone Cmpd. 7 | naloxone Cmpd. 7 |
| --- | --- | --- | --- | --- | --- | --- |
| Dose of Cmpd. 7 | — | — | 2.0 | 8.0 | 2.0 | 8.0 |
| BP | 109 ± 5 | 103 ± 5 | 88 ± 4* | 88 ± 5* | 75 ± 5* | 80 ± 3* |
| HR | 377 ± 12 | 379 ± 6 | 356 ± 16* | 331 ± 11* | 298 ± 9* | 353 ± 12 |
| PR | 53 ± 1 | 57 ± 1* | 53 ± 2 | 62 ± 2* | 57 ± 2 | 58 ± 1* |
| QRS | 28 ± 1 | 29 ± 1 | 31 ± 1* | 32 ± 1* | 33 ± 1* | 32 ± 1* |
| QT | 38 ± 1 | 41 ± 1 | 37 ± 1 | 42 ± 0.5* | 41 ± 1 | 41 ± 0.5* |

EXAMPLE 21

The procedures of Example 20 were carried out in respect of various doses of compound 10, compound 7, and U-50, 488H. Table 3 describes the results of the tests as $ED_{20}$ (μmol/kg) which are the doses required to produce a 20% change in the indice measured. The increases in P-R interval and QRS interval indicate cardiac sodium channel blockade while the increase in Q–T interval indicates ancillary cardiac potassium channel blockade which is the property of a type Ia antiarrhythmic. The electrophysiological effects of compound 10 and compound 7 occur very rapidly, generally achieving a maximum effect in one circulation time.

Similar results have been obtained in primates, wherein compound 1 appears to be equipotent to compound 10 and compound 7.

17

TABLE 3

|  |  | Cmpd. 10 | Cmpd. 7 | U-50,488H |
|---|---|---|---|---|
| EKG P-R | interval increase | 10 | 16 | 16 |
| EKG QRS | interval increase | >32 | >32 | 32 |
| EKG Q-T | interval increase | 32 | >32 | 32 |

EXAMPLE 22

Rats were prepared according to the preceding procedures, but without the coronary artery occlusion. Two Teflon coated silver wires stimulating electrodes were inserted through the chest wall and implanted in the left ventricle. Square wave stimulation was used to determine threshold current for capture, ventricular fibrillation threshold current, and effective refractory period (Howard, P. G. and Walker, M. J. A. (1990) Proc. West. Pharmacol. Soc., 33:123–127). Intracellular action potential duration and rise rate was determined according to the methods described in Abraham, et al., (1990) J. Pharmacol. Exp. Ther., 251:1166–1173. Table 4 contains $ED_{20}$ values (μmol/kg/min) for these indices of cardiac sodium channel blockage in respect of the named compounds. The increases in refractoriness and action potential duration indicate ancillary blockade of potassium channels. The effect on action potential rise rate by compound 1 is indicative of cardiac sodium channel blockade.

TABLE 4

| Compound | Threshold current increase | Fibrillation current increase | Refractoriness increase |
|---|---|---|---|
| 1 | 0.3 | 0.3 | 0.3 |
| 2 | 0.2 | 0.2 | 0.4 |
| 3 | 0.2 | 0.2 | 0.4 |
| 4 | 0.4 | 0.7 | 1 |
| 5 | 1 | 0.3 | 0.6 |
| 7 | 8 | 8 | 10 |
| 8 | 2 | 1 | 2 |
| 9 | 0.3 | 0.3 | 0.3 |
| 10 | 1 | 1 | 10 |
| U-50, 488H | 16 | 16 | 10 |

EXAMPLE 23

In order to directly measure cardiac sodium channel blockade, standard whole cell voltage clamp tests were carried out using single isolated adult rat cardiac cells. The tests were carried out in the presence of naloxone which blocked kappa opioid activity of the compounds being tested. Results in the form of $EC_{20}$ values, which are micromolar concentrations required to produce a 20% change in activity, are presented in Table 5. These results show that compound 1 is a potent sodium channel blocker like compound 7. Similar whole cell voltage clamp analysis with compound 1 demonstrated an effect on potassium current indicative of blockade at an $EC_{20}$ of 100 μmolar.

TABLE 5

| Compound | Sodium current reduction |
|---|---|
| 1 | 4 |
| 2 | 2 |
| 6 | 13 |
| 7 | 10 |

18

TABLE 5-continued

| Compound | Sodium current reduction |
|---|---|
| 8 | 4 |
| 9 | 4 |

EXAMPLE 24

The guinea pig intradermal wheal assay for local anaesthesia was carried out. The test consisted of injecting intradermally a small volume of approximately 0.1 ml of the test compound at various concentrations in a saline vehicle into the back of guinea pig, after which local anaesthesia was determined by the absence of a flinch upon pin prick near the site of injection. In this test, $ED_{20}$ values for compound 1; compound 7; and U-50,488H were 0.3, 0.5, and >0.5 percent (g/100 ml), respectively.

From the foregoing, it will be evident that, although specific embodiments of the invention have been described herein for purposes of illustration, various modifications may be made without deviating from the spirit and scope of the invention.

We claim:

1. A method for treating cardiac arrhythmias or inducing local anesthesia in a patient in need thereof by blocking sodium channels in cardiac or neuronal tissue, respectively comprising administering to said patient, by oral or parenteral administration for cardiac arrhythmias or by local injection or topical administration for local anesthesia, an effective amount of an enantiomer or geometric isomer of a compound of formula I, or a pharmaceutically acceptable salt thereof, said compound of the formula:

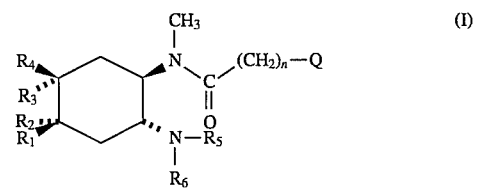

(I)

wherein n is either 0 or 1; $R_1$, $R_2$, $R_3$, $R_4$ are hydrogen hydroxy, alkoxy of from one to four carbon atoms, or points of attachment of a spiro- or fused five- or six-membered heterocyclic ring containing one oxygen or sulfur atom; $R_5$ and $R_6$ are either alkyl of from one to five carbon atoms or alkoxyalkyl of from two to five carbon atoms, or when taken together with the nitrogen atom to which they are attached, form a pyrrolidinyl, piperidinyl, morpholinyl, tetrahydroisoquinolinyl, or hexahydro-azepinyl ring; and Q is selected from the group consisting of 3,4,5-trimethylphenoxy;

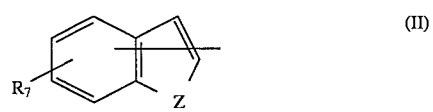

(II)

where $R_7$ is hydrogen, fluorine, chlorine, alkyl of from one to six carbon atoms, or aryl; Z is —$CH_2$—, —O—, —S—, or N—$R_8$ where $R_8$ is hydrogen, alkanoyl of from one to six carbon atoms, or alkyl of from one to six carbon atoms;

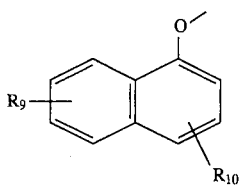

(III)

where $R_9$ and $R_{10}$ are independently hydrogen, fluorine, bromine, alkyl of from one to six carbon atoms, or alkoxy of from one to four carbon atoms;

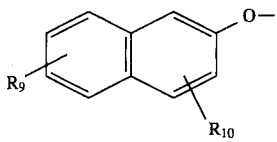

(IV)

where $R_9$ and $R_{10}$ are defined as above; and

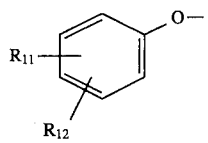

(V)

where $R_{11}$ and $R_{12}$ are independently hydrogen, fluorine, chlorine, bromine, nitro, trifluoromethyl, alkyl of from one to six carbon atoms, alkoxy of from one to six carbon atoms, or aryl.

2. The method of claim 1 wherein the stereoisomeric arrangement of the amine and amide bearing carbon atoms of the cyclohexyl ring of the compound formula I are as depicted in claim 1.

3. The method of claim 1 wherein n=1; $R_5$ and $R_6$ taken together with the nitrogen atom to which they are attached form a pyrrolidinyl ring; $R_3$ and $R_4$ are hydrogen; $R_1$ and $R_2$ are selected from the group consisting of hydrogen and an oxaspiran ring; and Q is selected from the group consisting of substituents II, III, and IV.

4. The method of claim 3 wherein Q is substituent II.

5. The method of claim 2 wherein n=1; $R_5$ and $R_6$ taken together with the nitrogen atom to which they are attached form a pyrrolidinyl ring; $R_3$ and $R_4$ are hydrogen; $R_1$ and $R_2$ are selected from the group consisting of hydrogen and points of attachment of an oxaspiran ring; and Q is selected from the group consisting of substituents II, III and IV.

6. The method of claim 5 wherein Q is substituent II.

7. The method of claim 1 wherein the compound is selected from the group consisting of:
(±)-trans-N-methyl-N-[2-(1-pyrrolidinyl)cyclohexyl]benzo[b]thiophene-4-acetamide;
(1R,2R)-(+)-N-methyl-N-[2-(1-pyrrolidinyl)cyclohexyl] benzo[b]thiophene-4-acetamide;
[(±)-(1α,2β,4β,5β)]-N-methyl-N-[4,5-dimethoxy-2-(1 -pyrrolidinyl)cyclohexyl]benzo[b]thiophene-4-acetamide;
[(±)-(1α,2β,4β,5β)]-N-methyl-N-[4,5-dimethoxy-2 -(1-pyrrolidinyl)cyclohexyl](3,4-dichlorophenoxy)acetamide;
(±)-trans-N-methyl-N-[2-(1-hexahydroazepinyl)cyclohexyl](3,4-dichlorophenoxy)acetamide
(±)-trans-N-methyl-N-[7-(1-pyrrolidinyl)-1 -oxaspiro [4.5] dec-8-yl]benzo[b]furan-4-acetamide;
[5R (5α,7α,8β)]-N-methyl-N-[7-(1-pyrrolidinyl)-1 -oxaspiro[4.5]dec-8-yl]benzo[b]furan-4-acetamide;
(±)-trans-N-methyl-N-[2-(1-pyrrolidinyl)cyclohexyl](3,4-dichlorophenoxy)acetamide;
(±)-trans-N-methyl-N-[2-(1-pyrrolidinyl)cyclohexyl]benzo[b]thiophene-3-acetamide;
[5S(5α,7α,8α)]-N-methyl-N-[7-(1-pyrrolidinyl)-1 -oxaspiro[4.5]dec-8-yl]benzo[b]furan-4-acetamide;
(1S,2S)-2-(benzo[b]thiophen-4-yl)-N-methyl-N-[2 -(1-pyrrolidinyl)cyclohexyl]acetamide;
(1R,2R)-2-(indol-3-yl)-N-methyl-N-[2-(1-pyrrolidinyl)cyclohexyl]acetamide;
(1S,2S)-2-(indol-3-yl)-N-methyl-N-[2-(1-pyrrolidinyl)cyclohexyl]acetamide;
(1R,2R)-2-(2,3-dichlorophenoxy)-N-methyl-N-[2 -(1-pyrrolidinyl)cyclohexyl]acetamide;
(1S,2S)-2-(2,3-dichlorophenoxy)-N-methyl-N-[2 -(1-pyrrolidinyl)cyclohexyl]acetamide;
(1R, 2R) -N-methyl-2-(1-naphthalenyloxy)-N-[2-(1-pyrrolidinyl)cyclohexyl]acetamide;
(1S,2S)-N-methyl-2-(1-naphthalenyloxy)-N-[2 -(1-pyrrolidinyl)cyclohexyl]acetamide;
[1S(1α,2β,4β)-N-methyl-N-[4-methoxy-2 -(1-pyrrolidinyl) cyclohexyl]benzo[b]furan-4-acetamide;
[1R(1α,2β,4β)-N-methyl-N-[4-methoxy-2 -(1-pyrrolidinyl) cyclohexyl]benzo[b]furan-4-acetamide;
(1R,2R)-inden-2-yl-N-methyl-N-[2-(1,1-dimethylamino)cyclohexyl]carboxamide; and
(1S,2S)-inden-2-yl-N-methyl-N-[2-(1,1-dimethylamino)cyclohexyl]carboxamide.

8. The method of claim 1 wherein the compound is selected from the group consisting of:
(±)-trans-N-methyl-N-[2-(1-pyrrolidinyl)cyclohexyl]benzo[b]thiophene-4-acetamide;
(1R,2R)-(±)-N-methyl-N-[2-(1-pyrrolidinyl)cyclohexyl] benzo[b]thiophene-4-acetamide;
[(±)-(1α,2β,4β,5β)]-N-methyl-N-[4,5-dimethoxy-2-(1-pyrrolidinyl)cyclohexyl]benzo[b] thiophene-4-acetamide;
(±)-(1α,2β,4β,5β)]-N-methyl-N-[4,5-dimethoxy-2-(1 -pyrrolidinyl)cyclohexyl](3,4-dichlorophenoxy)acetamide; and
(±)-trans-N-methyl-N-[2-(1-hexahydroazepinyl)cyclohexyl](3,4-dichlorophenoxy)acetamide.

9. The method of claim 1 wherein the compound is selected from the group consisting of:
[5S(5α,7α,8β)]-N-methyl-N-[7-(1-pyrrolidinyl)-1 -oxaspiro [4.5]dec-8-yl]-benzo[b]furan-4-acetamide;
(1S,2S)-2-(benzo[b]thiophen-4-yl)-N-methyl-N-[2 -(1-pyrrolidinyl)cyclohexyl]acetamide;
(1R,2R)-2-(indol-3-yl)-N-methyl-N-[2 -(1-pyrrolidinyl)cyclohexyl]acetamide;
(1R,2R)-2-(2,3-dichlorophenoxy)-N-methyl-N-[2-(1-pyrrolidinyl)cyclohexyl]acetamide;
(1R,2R)-N-methyl-2-(1-naphthalenyloxy)-N-[2-(1-pyrrolidinyl)cyclohexyl]acetamide;
[1S(1α,2β,4β)-N-methyl-N-[4-methoxy-2-(1-pyrrolidinyl) cyclohexyl]benzo[b]furan-4 -acetamide; and
(1R,2R)-inden-2-yl-N-methyl-N-[2-(1,1-dimethylamino)cyclohexyl]carboxamide.

10. The method of claim 1 wherein the compound is:
(±)-trans-N-methyl-N-[2-(1-pyrrolidinyl)cyclohexyl]benzo [b]thiophene-4-acetamide.

11. The method of claim 1 wherein the compound of formula I is:
(1R,2R)-(±)-N-methyl-N-[2-(1-pyrrolidinyl)cyclohexyl] benzo[b]thiophene-4-acetamide.

12. The method of claim 1 wherein the compound is:
[(±)-(1α,2β,4β,5β)]-N-methyl-N-[4,5-dimethoxy-2-(1 -pyrrolidinyl)cyclohexyl]benzo[b]thiophene-4-acetamide.

13. The method of claim 1 wherein the compound is:
[(±)-(1α,2β,4β,5β)]-N-methyl-N-[4,5-dimethoxy-2 -pyrrolidinyl)cyclohexyl](3,4-dichlorophenoxy)acetamide.

14. The method of claim 1 wherein the compound is:
(±)-trans-N-methyl-N-[2-(1-hexahydroazepinyl)cyclohexyl](3,4-dichlorophenoxy)acetamide.

15. The method of claim 1 wherein the sodium channels blocked are sodium channels in cardiac tissue.

* * * * *

UNITED STATES PATENT AND TRADEMARK OFFICE
CERTIFICATE OF CORRECTION

PATENT NO. : 5,506,257
DATED : April 9, 1996
INVENTOR(S) : Bernard A. MacLeod, et al It is certified that error appears in the above-indentified patent and that said Letters Patent is hereby corrected as shown below:

In column 18, claim 1, line 31, following "respectively", please insert--,--.

In column 18, claim 1, line 47, following "hydrogen", please insert--,--.

In column 19, claim 7, line 55, following " acetamide", please insert--;--.

In column 19, claim 7, line 64, please delete "8α" and insert therefor--8β--.

In column 20, claim 8, line 24, following "(1R,2R)-", please delete "(±)" and insert therefor--(+)--.

In column 20, claim 8, line 28, before "(±)", please insert--[--.

In column 20, claim 11, line 54, following "(1R,2R)-", please delete "(±)" and insert therefor--(+)--.

UNITED STATES PATENT AND TRADEMARK OFFICE
CERTIFICATE OF CORRECTION

PATENT NO.   : 5,506,257
DATED        : April 9, 1996
INVENTOR(S)  : Bernard A. MacLeod, et al It is certified that error appears in the above-indentified patent and that said Letters Patent is hereby corrected as shown below:

Column 20, claim 13, line 59, following "dimethoxy-2", insert-- -(1 --.

Signed and Sealed this

Thirteenth Day of August, 1996

Attest:

BRUCE LEHMAN

*Attesting Officer*      *Commissioner of Patents and Trademarks*